(12) United States Patent
Bombach et al.

(10) Patent No.: US 8,092,763 B2
(45) Date of Patent: Jan. 10, 2012

(54) APPARATUS FOR POSITIONING A CUVETTE IN AN OPTICAL BEAM PATH OF AN OPTICAL MEASURING INSTRUMENT

(75) Inventors: Andreas Bombach, Stelle (DE); Peter Scheffler, Hamburg (DE)

(73) Assignee: Eppendorf AG, Hamburg (DE)

( * ) Notice: Subject to any disclaimer, the term of this patent is extended or adjusted under 35 U.S.C. 154(b) by 479 days.

(21) Appl. No.: 12/276,922

(22) Filed: Nov. 24, 2008

(65) Prior Publication Data
US 2009/0237655 A1    Sep. 24, 2009

(30) Foreign Application Priority Data
Nov. 30, 2007   (DE) .......................... 10 2007 058 806

(51) Int. Cl.
*B01L 9/00* (2006.01)
*G01N 21/01* (2006.01)

(52) U.S. Cl. ........ 422/562; 422/401; 422/403; 356/244; 356/246

(58) Field of Classification Search .................... None
See application file for complete search history.

(56) References Cited

U.S. PATENT DOCUMENTS

| | | | |
|---|---|---|---|
| 3,711,201 A * | 1/1973 | Sturlese et al. | 356/313 |
| 3,977,794 A * | 8/1976 | Liedholz | 356/244 |
| 2005/0281715 A1* | 12/2005 | Jacobs et al. | 422/104 |
| 2006/0028071 A1* | 2/2006 | Chang et al. | 310/12 |
| 2007/0041877 A1* | 2/2007 | Maurer et al. | 422/102 |

* cited by examiner

*Primary Examiner* — P. Kathryn Wright
(74) *Attorney, Agent, or Firm* — Vidas, Arrett & Steinkraus, P.A.

(57) ABSTRACT

An apparatus for positioning a cuvette in an optical beam path of an optical measuring instrument, with a shaft for axially inserting a cuvette, and means for pressing a cuvette against at least one wall surface of the shaft, which comprise at least one arrangement of a magnet, stationarily arranged with respect to the shaft, and a magnet movable with respect to the same, which are oriented such that the movable magnet tends to occupy a certain position with respect to the stationary magnet, in which the movable magnet engages at least partially into the shaft.

7 Claims, 3 Drawing Sheets

APPARATUS FOR POSITIONING A CUVETTE IN AN OPTICAL BEAM PATH OF AN OPTICAL MEASURING INSTRUMENT

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to an apparatus for positioning a cuvette in an optical beam path of an optical measuring instrument.

For the analysis in spectrometers or photometers or other optical measuring instruments, liquid samples are filled into cuvettes. The cuvettes have planar parallel side walls for the passage of the light beam. They have to be positioned very accurately in the optical beam path of the optical measuring instrument in order to obtain the measuring results with small systematic and random measurement deviations. For this purpose, the optical measuring instruments have cuvette shafts, (called only "shafts" in the following, where shaft is defined as a passageway for axially receiving a cuvette), through which the optical beam path passes through crosswise. By axially inserting them up to the bottom of the shaft, the cuvettes can be brought into the desired position in the optical beam path. Mostly, the shaft has a rectangular cross section for accommodating cuvettes with a box-like cross section. Most current spectrometers and photometers have a shaft with a cross section of 12.3 mm×12.5 mm. The heights of the light beam above the bottom of the shaft vary from 8.5 mm to 20 mm, depending on the apparatus. In "standard cuvettes", the cross section and the height are adapted to the above mentioned dimensions of the shafts of most of the current optical measuring instruments.

Cuvettes for one single use ("single-use cuvettes") have strong deviations in dimensions and weight. This applies for the outer dimensions in particular. These deviations negatively affect the accuracy of the positioning of the cuvettes in the shaft of an optical measuring instrument.

In a known photometer, a metal-made roller is pressed against an edge of the cuvette in a passage opening of the wall of the shaft by a spiral spring. Through this, the cuvette is set into a defined bearing against the wall of the shaft, and the precision of the positioning in the optical beam path is improved. When the cuvette is introduced into the shaft, the roller is deflected somewhat laterally against the elastic restoring force of the spiral spring. In a manual operation, this requires a certain expenditure of force by the user. Furthermore, the spring force may deform the cuvette, through which the positioning accuracy can be affected. With cuvettes made of plastics, wear by friction may occur in addition. Cuvettes made of quartz glass are brittle and they may crack out or break due to the load.

Starting from this, the present invention is based on the objective to provide an apparatus for positioning a cuvette in an optical beam path of an optical measuring instrument, which facilitates the use, improves the positioning accuracy and imparts fewer loads to the cuvettes.

BRIEF SUMMARY OF THE INVENTION

The apparatus according to the present invention for positioning a cuvette in an optical beam path of an optical measuring instrument has: a shaft for axially inserting a cuvette, and means for pressing the cuvette against at least one wall surface of the shaft, which comprise at least one arrangement of a magnet, stationarily arranged with respect to the shaft, and a magnet movable with respect to this, which are oriented such that the movable magnet tends to occupy a certain position with respect to the stationary magnet, in which the movable magnet engages at least partially into the shaft.

In the apparatus according to the present invention, the optical beam path or the light beam, respectively, passes transversely through the shaft. The outer dimensions of the cuvette are matched to the inner dimensions of the shaft in a known manner. Preferably, the shaft has the ordinary dimensions for standard cuvettes. When no cuvette is inserted into the shaft, the movable magnet occupies the certain position with respect to the stationary magnet. In this, the movable magnet engages at least partially into the shaft. In the insertion into the shaft, the cuvette hits the movable magnet. The movable magnet avoids the cuvette, wherein however, it has the tendency to revert into the certain position due to the magnetic forces acting between the movable magnet and the stationarily arranged magnet. As a result, the movable magnet exerts a force on the cuvette. Through this force, the cuvette is pressed against at least one wall surface of the shaft. Through this, a reproducible, accurate positioning of the cuvette is achieved.

This positioning takes place in a particularly smooth manner. Namely, in difference to the conventional apparatus, in which the roller on the spiral spring can evade only transversely to the axis of introduction of the cuvette, the movable magnet can evade in the direction transversely to the axis of introduction and in the direction of the axis of introduction. Evasion movements are possible in all the directions which lay in a plane which is defined by the evasion movements transversely to the axis of introduction and in the direction of the axis of introduction. The additional degree of freedom of the evasion movement leads to a smoother insertion of the cuvettes. The contact between cuvette and movable magnet is soft, and thus it is gentler for the cuvettes than in the conventional apparatus. Frictional wear and damage of the cuvettes are avoided. Due to the gentle introduction of forces, the deformation of the cuvettes is reduced and the positioning accuracy is improved through this. Due to the occurrence of frictional wear or due to the smaller occurrence of frictional wear, respectively, or of dirt, respectively, in the cuvette shaft and due to the improved positioning, the measuring accuracy of the optical measuring instrument is improved. Further, the space requirements for the magnets are smaller than that for the roller with a spiral spring in the conventional apparatus. Also, the installation of the magnet arrangement is less sumptuous than the installation of the roller with a spiral spring.

The shaft can be defined by walls or by other means, which delimit the same entirely or partially. It is not necessary that the means for delimiting the shaft completely close up the same laterally. For the optical beam path in particular, the shaft may feature passage openings. According to one embodiment, the shaft has at least two adjacent wall surfaces which are oriented orthogonal with respect to each other. The same can delimit two sides of a shaft with a square cross section. The remaining delimitations of the shaft can be formed by the means for pressing on the cuvette, which press a cuvette against the two wall surfaces which are oriented orthogonal with respect to each other. For this purpose, the means for pressing on can be arranged diametrically opposite to a corner between the two wall surfaces which are oriented orthogonal with respect to each other.

According to a further embodiment, the means for delimiting the shaft have three or four wall surfaces, wherein two adjacent wall surfaces at a time are oriented orthogonal with respect to each other. A shaft with square cross section can be entirely or partially delimited laterally by three or four wall surfaces. In the case that the wall surfaces embrace the shaft laterally completely, they can feature a passage opening for the movable magnet.

According to one embodiment, the shaft is present in a housing or in a part of a housing. For instance, the shaft is formed as a break through or a recess of a massive housing wall, or as a box-shaped top on a housing wall.

In principle, the apparatus can have plural movable magnets, which act in different in and/or in the same direction(s) on a cuvette which is set into the shaft. For instance, two movable magnets can be arranged on adjacent sides of the shaft which are oriented orthogonal with respect to each other, so that they press against opposing side walls of a cuvette with rectangular cross section, in order to press the opposing side walls of the cuvette against the adjacent wall surfaces of the shaft. According to a preferred embodiment, the movable magnet engages into the shaft on a corner of the shaft. As a consequence, the movable magnet presses against a corner of a cuvette which is set in and presses the same against the diametrically opposing corner or the adjacent wall surfaces of the shaft, respectively. This apparatus favours a reproducible, accurate positioning and requires only one arrangement of a movable magnet and a stationary magnet.

In principle, it is also possible to arrange plural arrangements of a movable magnet and a stationary magnet on the shaft, distributed in the direction of insertion of the cuvette.

The movable and the stationary magnet can be formed differently. According to a preferred embodiment, the stationary and/or the movable magnet have a cylindrical and/or an annular cross section. A cylindrical or annular movable magnet has the advantage that the movable magnet can roll along on the shell of the cuvette, through which the same can be inserted even more smoothly.

The magnets may be electric magnets. Preferably, they are permanent magnets. These are made of metal alloys from iron, nickel and aluminium, with admixtures of cobalt, manganese and copper, for instance. Exceptionally strong magnets made of "rare earths" can also be used, like of samarium-cobalt or neodym-iron-bor, for instance.

For a particularly smooth insertion of a cuvette into the shaft, according to a further embodiment, the movable magnet features a rotatably mounted roller, which engages into the shaft which is delimited by the means for delimiting. When a cuvette is inserted, the roll rolls off on the shell of the cuvette, so that friction and frictional wear are reduced further. According to one embodiment, the movable magnet features a pin for bearing the roller, on which the roller is rotatably mounted. According to a further embodiment, the roller is made of a plastic material. Through this, the friction between the roller and the cuvette can be reduced further.

Finally, according to a further embodiment, the movable magnet is arranged in a free space of a housing, which permits a movement with respect to the stationary magnet in the direction of the shaft and crosswise thereto. According to a further embodiment, the free space has delimitations, which prevent the stationary magnet from being removed so far from the movable magnet that it cannot arrive in the certain position automatically.

BRIEF DESCRIPTION OF THE SEVERAL VIEWS OF THE DRAWINGS

In the following, the present invention is explained in more detail by means of the attached drawings of examples of its realisation. In the drawings show.

DETAILED DESCRIPTION OF THE INVENTION

Figure 1:
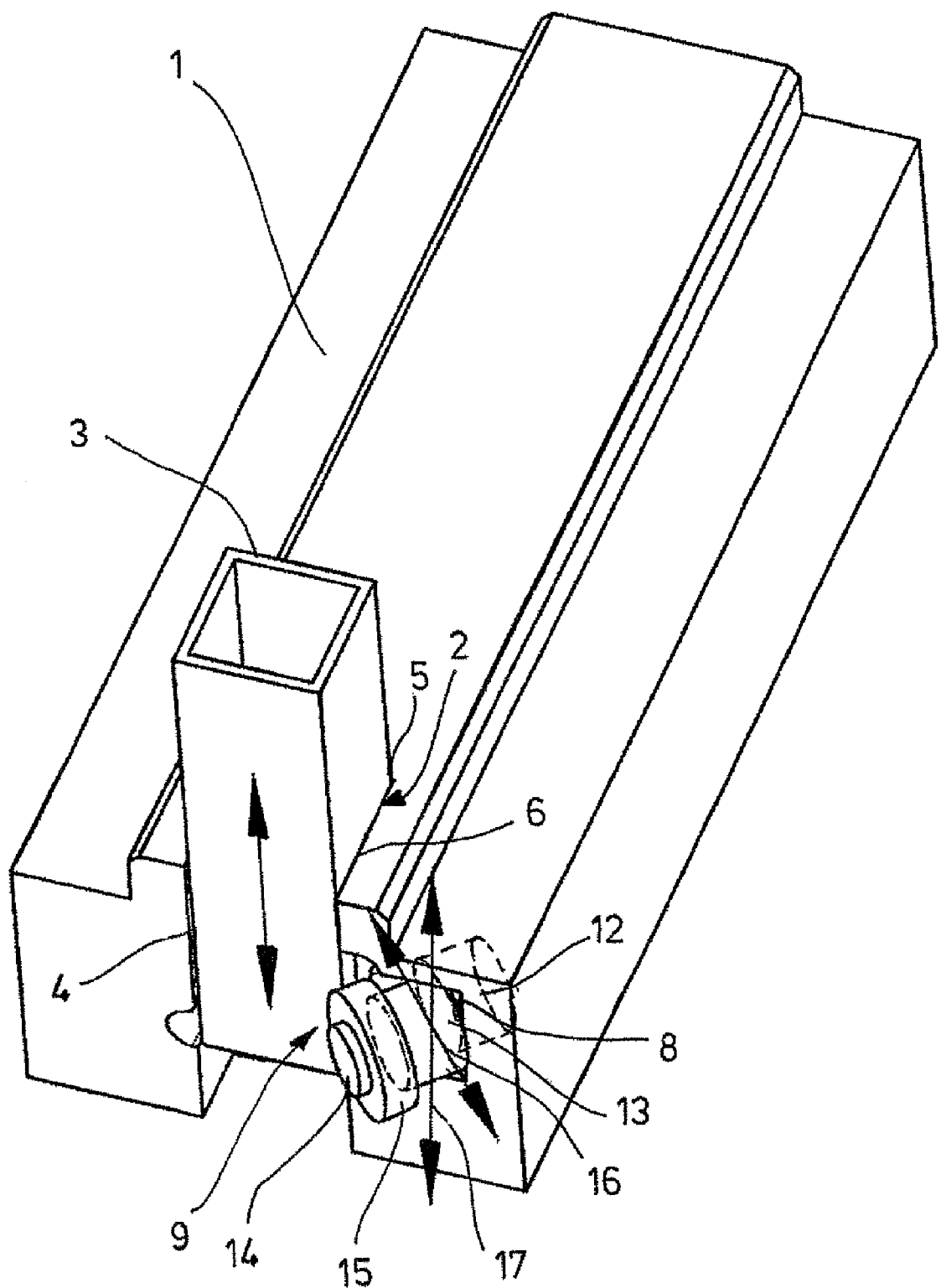
FIG. 1 an apparatus with the front wall of the shaft taken off, the cuvette being inserted, in a perspective view skew from the top side and from the right side.
Figure 2:
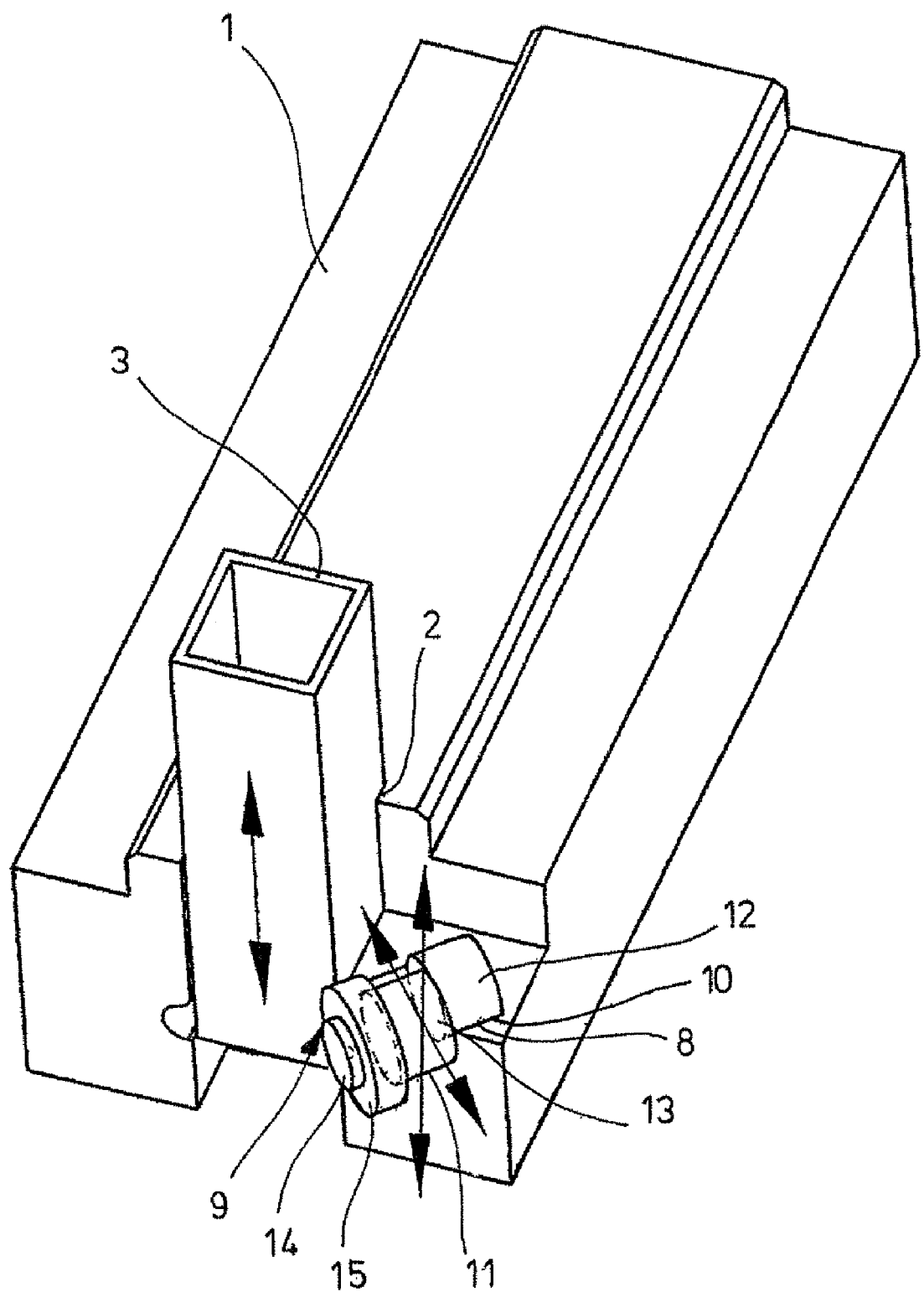
FIG. 2 the same apparatus with free cut attachment area of the stationary magnet, in the same perspective view.
Figure 3:
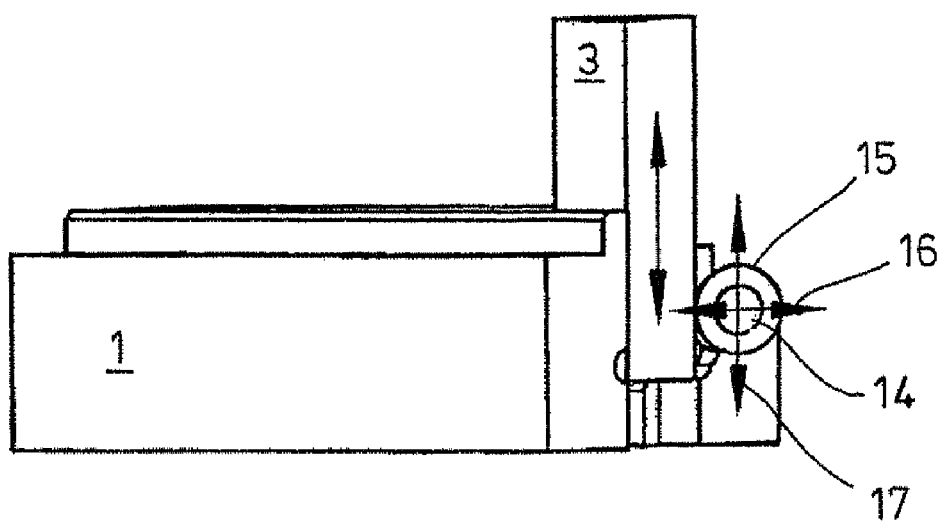
FIG. 3 the same apparatus in a perspective view from the front side and from the left side.
Figure 4:
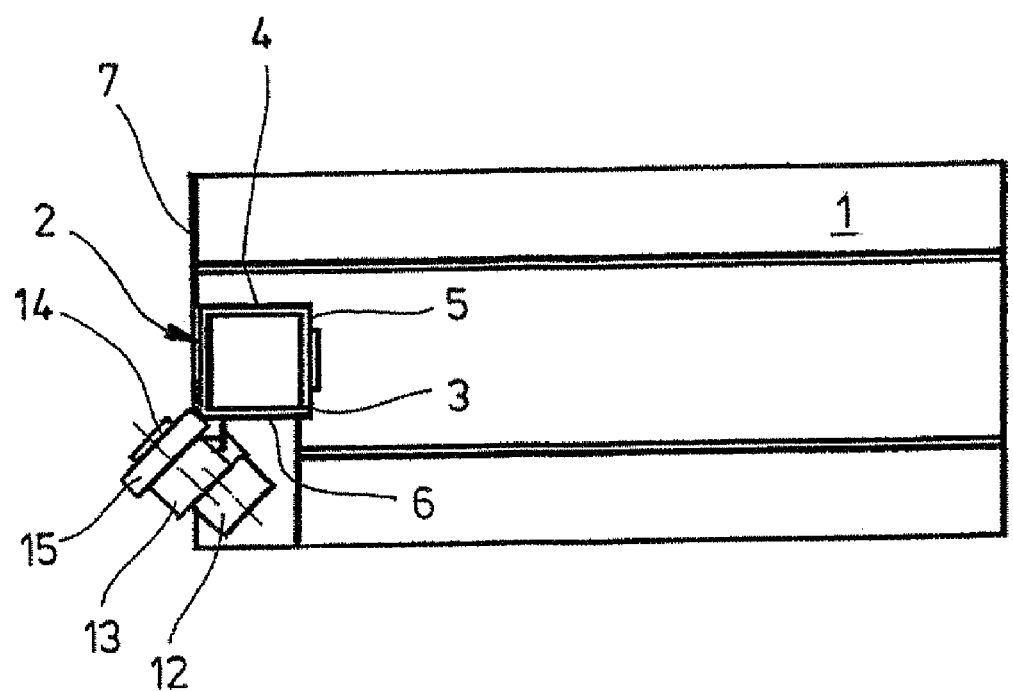
FIG. 4 the same apparatus in a top view.

While this invention may be embodied in many different forms, there are described in detail herein a specific preferred embodiment of the invention. This description is an exemplification of the principles of the invention and is not intended to limit the invention to the particular embodiment illustrated The apparatus according to present invention has a housing 1, which is depicted only in parts in the figures. In the housing 1 is formed a shaft 2 for axially inserting a box-shaped cuvette 3. The shaft 2 has three wall surfaces 4, 5, 6 in the housing 1, wherein wall surfaces 4, 5, 6, each one adjacent to another, are oriented orthogonal to each other. A fourth wall surface for delimiting the shaft 2 is formed by a plate, which is screwed up on the front side of the housing 1 and which is not depicted in the FIGS. 1 to 3. In FIG. 4, this wall surface is indicated by the reference numeral 7.

The housing 1 has a recess 8 with a passage opening 9 towards the shaft 2. The recess 8 has a cylindrical portion 10 with a smaller diameter, and a further cylindrical portion 11 with a greater diameter, which are adjacent to each other. The further cylindrical portion 11 is arranged alongside to the passage opening 9, and the cylindrical portion 10 is arranged deeper in the housing 1. The cylindrical portions 9, 11 have coaxial centre axes. The centre axes of the cylindrical portions 10, 11 are oriented vertically to a diagonal line through the shaft 2.

A magnet 12 is arranged in the cylindrical portion 10. The magnet 12 is pressed into the cylindrical portion 10 and/or glued in therein, so that it is stationarily arranged in the housing 1. The cylindrical magnet 12 is dimensioned such that it projects somewhat into the further cylindrical portion 11.

A movable magnet 13 is arranged in the cylindrical portion 11. The diameter of the movable magnet 13 corresponds to the diameter of the stationary magnet 12. The magnets 12, 13 have their poles on the front sides. They bear against each other with opposite poles on the flat front sides which face each other.

As the magnet 13 is arranged in the portion 10 of the recess 8 with the greater diameter, it is laterally movable with respect to the magnet 12. However, the movable magnet 13 tends to orient its axis coaxially to the axis of the magnet 12.

The movable magnet 13 carries a pin 14, which is glued on the magnet 13, for instance. A roller 15 made of plastic material is rotatably mounted on the pin 14. The outer diameter of the roller 15 is selected such that the roller 15 partly projects into the shaft 2.

When a cuvette 3 is inserted into the shaft 2, the cuvette 3 hits the roller 15. As a consequence, the movable magnet 13 evades crosswise to the axis of the shaft 2 in the direction 16, and/or in the direction 17 of the axis of the shaft 2. The movable magnet 13 has the tendency to revert into its starting position, so that the roller 15 presses against the wall surfaces 4, 5. When the cuvette 3 is thrust into the shaft 2 up to against a—not shown—bottom or lower stop, it is held fast in a defined position on the wall surfaces 4, 5 by the roller 15 as a consequence of this.

The roller 15 can evade in two directions 16, 17 or in the plane spanned up by these directions, respectively. Due to the smooth evasion movement of the magnet 13, the position fixing is gentler for the cuvettes 3 than in conventional positioning devices. In addition, the cuvettes 3 are stress loaded only gently, because the roller 15 rolls off on the cuvette 2 in the insertion. When a roller 15 made of plastic material is used, the load stresses on the cuvette and frictional wear or damages connected with this are reduced further.

When the cuvette 3 is pulled out of the shaft 2, the movable magnet 13 reverts automatically into its starting position, in which the magnets 12, 13 are arranged coaxially with respect to each other. The shaft 2 is then ready to accept another cuvette 3.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An apparatus for positioning a cuvette in an optical beam path of an optical measuring device, comprising:
   a housing, the housing including a shaft for axially receiving the cuvette and a recess, the shaft being defined by a plurality of wall surfaces in the housing;
   a fixed magnet disposed in the recess;
   a movable magnet magnetically connected with the fixed magnet, in a normally aligned position;
   a roller connected to the movable magnet,
   whereby when the cuvette axially moves in the shaft such that the roller moves the movable magnet laterally relative to the fixed magnet, the magnetic force between the fixed magnet and movable magnet, which urges the moveable magnet towards its normally aligned position, exerts a pressing force against the cuvette, so that the cuvette is pressed against at least one of the plurality of wall surfaces defining the shaft.

2. The apparatus according to claim 1, wherein the plurality of wall surfaces include at least two wall surfaces, which are adjacent and oriented orthogonal to each other.

3. The apparatus according to claim 1, wherein the movable magnet engages into the shaft on a corner of the shaft, as the cuvette moves the movable magnet relative to the fixed magnet, the magnet force between the fixed and movable magnets presses the cuvette into at least one wall surface of the shaft.

4. The apparatus according to claim 1, wherein the fixed and/or the movable magnet have a cylindrical and/or circular cross section.

5. An The apparatus according to claim 1, wherein the movable magnet features a pin, on which the roller is rotatably mounted.

6. The apparatus according to claim 2, wherein the roller is made of a plastic material.

7. The apparatus according to claim 1, wherein the movable magnet is arranged in a free space of a housing, which permits a movement with respect to the fixed magnet in the direction of the shaft and crosswise thereto.

* * * * *